United States Patent
Elliott (10) Patent No.: US 11,890,220 B1
(45) Date of Patent: Feb. 6, 2024

(54) EXTERNAL MALE CATHETER WITH SUCTION CONNECTION

(71) Applicant: Mary M. Elliott, Sault Ste. Marie, MI (US)

(72) Inventor: Mary M. Elliott, Sault Ste. Marie, MI (US)

(*) Notice: Subject to any disclaimer, the term of this patent is extended or adjusted under 35 U.S.C. 154(b) by 0 days.

(21) Appl. No.: 17/493,439

(22) Filed: Oct. 4, 2021

Related U.S. Application Data (60) Provisional application No. 63/087,498, filed on Oct. 5, 2020.

(51) Int. Cl.
*A61F 5/453* (2006.01)
*A61M 1/00* (2006.01)
*A61F 5/44* (2006.01)

(52) U.S. Cl.
CPC ............ *A61F 5/453* (2013.01); *A61F 5/4405* (2013.01); *A61M 1/71* (2021.05)

(58) Field of Classification Search
CPC ...... A61F 5/453; A61F 5/4408; A61F 5/4405; A61B 5/6834
See application file for complete search history.

(56) References Cited

U.S. PATENT DOCUMENTS

| | | | |
|---|---|---|---|
| 3,421,504 A | | 1/1969 | Gibbons |
| 3,421,507 A | | 1/1969 | Gresham |
| 4,239,044 A | * | 12/1980 | Pavlinch ................. A61F 5/453 600/580 |
| 4,655,755 A | * | 4/1987 | Ruffini .................... A61F 5/453 604/352 |
| 4,957,487 A | | 9/1990 | Gerow |
| 5,499,977 A | | 3/1996 | Marx |
| 5,618,277 A | | 4/1997 | Goulter |
| 5,662,631 A | | 9/1997 | Marx |
| 2006/0004332 A1 | * | 1/2006 | Marx ...................... A61F 5/453 604/347 |
| 2019/0091059 A1 | * | 3/2019 | Gabriel ................. A61F 5/4405 |

FOREIGN PATENT DOCUMENTS

| | | | | |
|---|---|---|---|---|
| GB | 2198952 A | * | 6/1988 | ............. A61F 5/453 |
| WO | WO-2013117635 A1 | * | 8/2013 | ............. A61F 5/453 |

OTHER PUBLICATIONS

Amazon, "Conveen Optima Male External Catheter, Self-Adhering, Double-Grip Strip, Silicone, 35mm Standard Length 22035 (Box of 30)," https://amazon.com/Conveen-External-Catheter-Self-Adhering-Double-Grip/dp/B07DTF1BTF.

* cited by examiner

*Primary Examiner* — Catharine L Anderson
*Assistant Examiner* — Arjuna P Chatrathi
(74) *Attorney, Agent, or Firm* — Mitchell Intellectual Property Law, PLLC (57) ABSTRACT

An external male catheter comprising an inner drainage sheath configured to unrolled and fitted over a penis like a condom, and an attached outer suction sheath configured to be unrolled over the fitted drainage sheath. A one-way drainage port extends from the inner drainage sheath through the outer suction sheath in fluid-tight manner, and a one-way suction port extends from the outer suction sheath. Suction is selectively applied to both the drainage and suction ports as the catheter is applied, in order to assist with fitting and retention of the catheter.

3 Claims, 7 Drawing Sheets

EXTERNAL MALE CATHETER WITH SUCTION CONNECTION

RELATED APPLICATIONS/PRIORITY BENEFIT CLAIM

This patent application claims priority to provisional application Ser. No. 63/087,498 filed Oct. 5, 2020, entitled EXTERNAL MALE CATHETER WITH SUCTION CONNECTION.

FIELD

The subject matter of the present application is in the field of external male catheters.

BACKGROUND

External male catheters are urine-collecting devices used in hospitals, in nursing homes, and in home medical care for male patients, who because of limited mobility, are unable to use a toilet. The typical male catheter has a condom-like sheath that fits over the penis, and a drain tube leading from the body to a collection receptacle, usually a fluid-collecting bag.

U.S. Pat. No. 3,421,504 to Gibbons shows an elongated sheath-like rubber body configured to fit over and contract about the penis. A flexible but stiff conduit communicates with the central end of the sheath and is communicated with a source of vacuum.

U.S. Pat. No. 3,421,507 to Gresham shows a male urinary drain comprising an elongated expansible receptable having a drain hose at one end and an attachment sheath foldable axially inwardly on itself to provide a double-walled attachment portion for snugly encasing a male urinary organ in water-tight engagement.

U.S. Pat. No. 4,957,487 to Gerow shows an external male urinary catheter system with a negative pressure evacuation device communicating with the sheath, the negative pressure causing the penis to elongate for fitting the sheath. The sheath includes a one-way drainage tube for evacuating urine to an evacuation device, and a one-way air tube for equalizing the negative pressure between the sheath and the evacuation device after urine has been voided.

U.S. Pat. No. 5,499,977 to Marx shows a male external catheter with vacuum assist. The catheter has a rolled up ring attached for securing it to the male organ, and an elongated hollow extension with annular grooves. A plastic tube removably receives the catheter, and the rolled up ring may roll atop the plastic tube for application to a user. A rubber bulb secured to the plastic tube functions as a vacuum for the user.

U.S. Pat. No. 5,618,277 to Goulter shows a condom catheter with a first sheath section and a second urine collecting compartment divided by a skin shield incorporating a soft thread-reinforced non-return, non-invertible valve. The collecting compartment has a twist-around drain valve or a ball-obturator drain valve. The skin shield can alternatively incorporate two non-return, non-inverting reinforced valves to eliminate pooling of urine.

U.S. Pat. No. 5,662,631 to Marx shows a male external catheter with a vacuum or reduced pressure producing means to aid in installation and retention. Reduced pressure is applied interiorly within a rigid catheter sleeve and a thin elastomeric sheath, which in turn covers and applies the reduced pressure to the penis of the wearer while maintained within the catheter sleeve during both installation and use. An optional centering ring surrounds an intermediate portion of the elastomeric sheath, and the reduced pressure means can be in valved communication with the interior of the sleeve outlet and the drainage tube.

U.S. Patent Application Publication No. 2006/0004332A1 to Marx shows a male condom urinary catheter with an interior surface and a thin cylindrical sheath of elastic material, an outlet for connection to a urine collecting device, and a neck coupled between the sheath and the outlet. A vacuum source is coupled to the catheter to draw the circumferential portion of the catheter interior against the head of the penis, the sheath is rolled onto the penis, and the vacuum is released.

None of the foregoing prior art devices is believed to provide the combination of ease of installation, comfort, and watertight sealing to make them truly useful in a hospital or home healthcare environment for nurses, caregivers, and wearers.

BRIEF SUMMARY

The present invention is an external male catheter and a method of use. In general the external male catheter comprises an inner drainage sheath configured to be fitted over the penis like a condom, and an attached outer suction sheath overlying and configured to surround and extend over and beyond the inner drainage sheath like a condom. Each of the inner and outer sheaths has its own one-way port extending and accessible from an upper end of the outer sheath.

In further form, the inner drainage sheath has a structured upper drainage end or "cap" with a one-way drainage port, and a soft, flexible rolled body portion configured to be unrolled downwardly a first length from the tip. The outer suction sheath has a structured upper end or cap above the tip of the inner sheath, with a one-way suction port and a soft, flexible rolled body portion configured to be unrolled downwardly a second length over and beyond the unrolled length of the inner sheath body. The suction port and the drainage port extend separately from the cap of the outer sheath, with the drainage port extending from the tip of the inner sheath outwardly through the cap of the outer sheath with a fluid-tight seal between them.

The inner drainage sheath and the outer suction sheath are preferably connected to one another, for example at the junction of the drainage port and the outer sheath cap, so that they are applied as a single unit.

In a related method of use, the external male catheter is applied to a patient by placing the drainage cap of the inner sheath over the head of the penis, and applying suction to the drainage port from a location external to the suction sheath with a suction device to draw the head of the penis securely into the drainage cap in proximity to the drainage port's inner end underneath the suction cap. The rolled body portion of the inner sheath is extended by unrolling it down the shaft of the penis a first lesser distance. The rolled body of the outer sheath is then unrolled down from the suction cap over the extended body of the inner sheath a second greater distance, and suction is applied to the suction port to further secure the penis inside the outer sheath so that both the outer sheath and the inner sheath remain firmly attached once suction is removed from the suction port. A catheter hose is attached to the outer end of the drainage port to communicate the interior of the drainage sheath cap to a remote urine collection receptacle.

DETAILED DESCRIPTION

Figure 1:
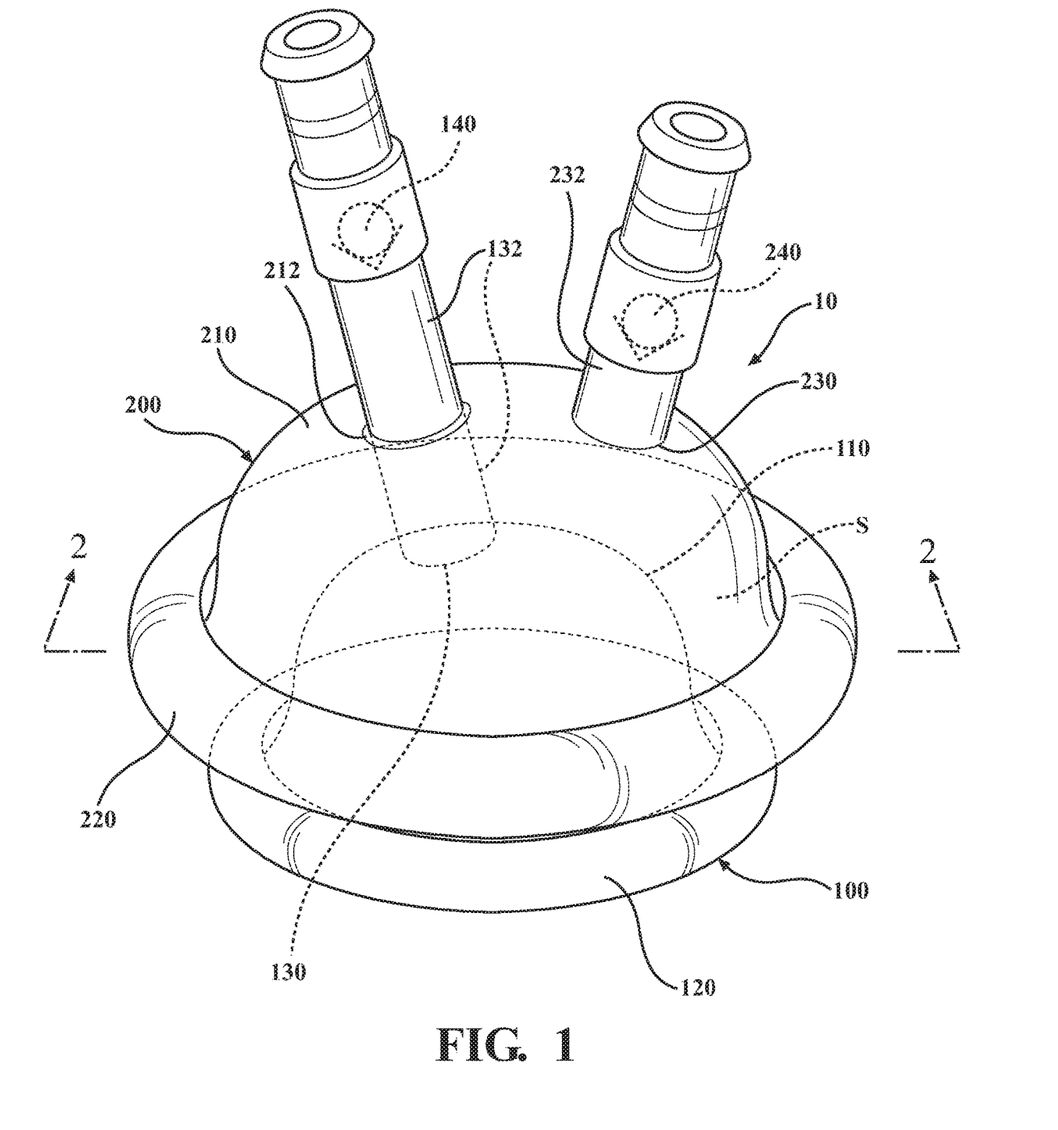
FIG. 1 is a perspective side view of an example external male catheter according to the invention, with body portions of the inner and outer sheath portions rolled up.
Figure 2:
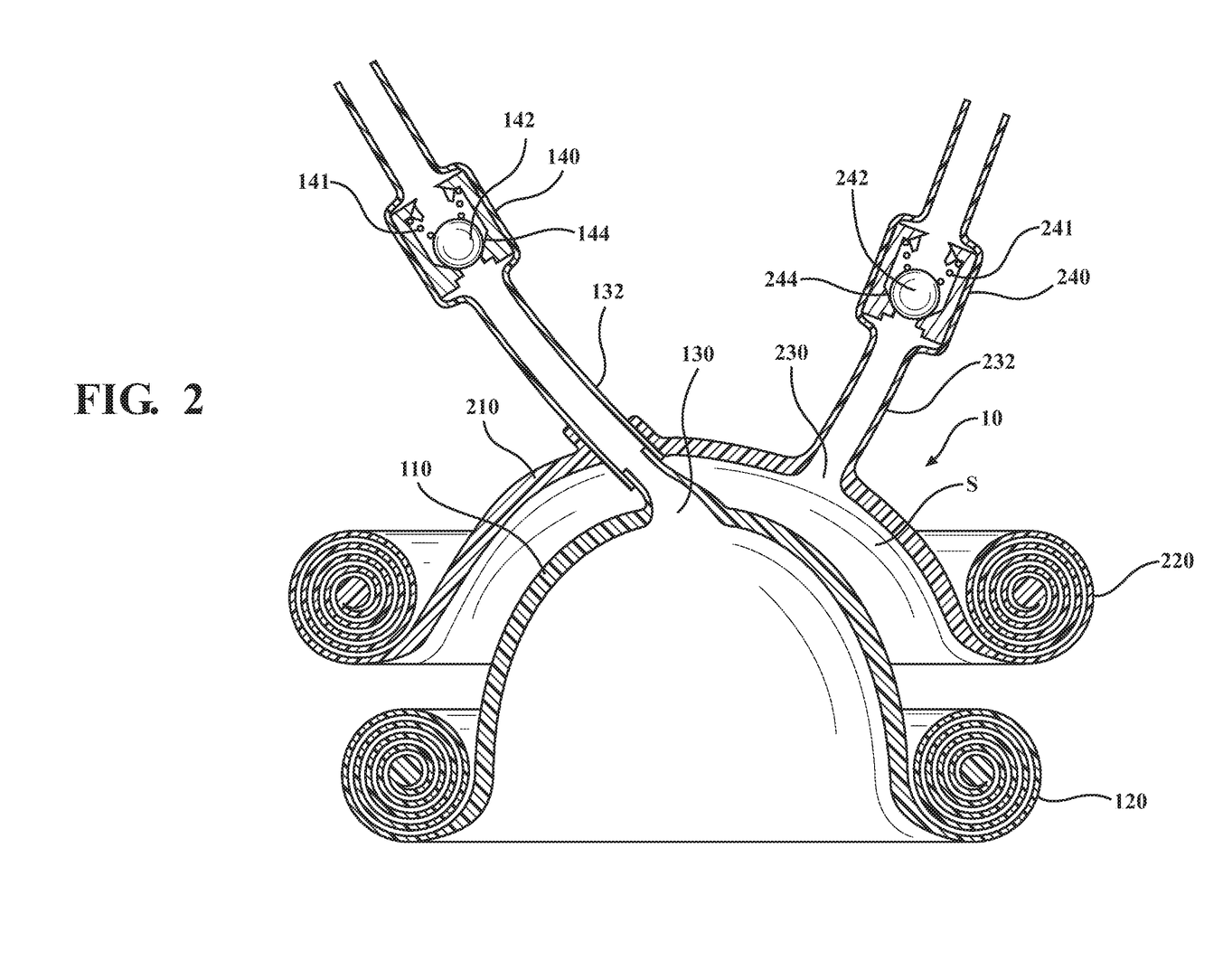
FIG. 2 is a side elevation section view of the device of FIG. 1.

Referring first to FIGS. 1 and 2, an external male catheter 10 is shown in exemplary form in order to teach how to make and use the claimed invention. Catheter 10 comprises an inner drainage sheath portion 100 and an outer suction sheath portion 200 joined to inner sheath 100 to be applied as a unit to a male patient. While the materials used for catheter 10 may vary, the inner and outer sheath portions 100, 200 are primarily made from a soft, strong, flexible, waterproof material known for use in "condom catheters", such as but not limited to latex, nitrile, or silicone rubber, or combinations thereof suitable for medical or patient care use. Inner sheath 100 and outersheath 200 may be formed from the same material, or may be formed from different materials or combinations of material, provided they function as described below. Those skilled in the art will be familiar with suitable material options and manufacturing methods.

Inner sheath 100 includes a preferably thicker, structured cap 110 at its upper or outer end, capable of maintaining its shape both before and after application, and a preferably thinner, more flexible, rolled body portion 120 circumferentially attached to the lower perimeter of cap 110, for example by being integrally molded therewith. A drainage port 130 is formed in the drainage cap 110, with a stem or tube or similar conduit structure 132 extending outwardly therefrom to provide a passageway through which urine can flow from the port 130 in the drainage cap 110 to a urine collection receptacle.

Outer sheath 200 includes a preferably thicker, more-structured cap 210 at its upper or outer end, capable of maintaining its shape both before and after application, and a preferably thinner, more flexible, rolled body portion 220 circumferentially attached to the lower perimeter of cap 210. Outer cap 210 is of greater diameter than the inner cap 110, so that it at least partly overlies and/or surrounds cap 110. A suction port 230 is formed in the outer cap 210, with a stem or tube or similar conduit structure 232 extending outwardly therefrom to provide a passageway through which suction can be applied to draw air through the port from the space S between outer sheath 200 and inner sheath 100 in a manner described in more detail below.

Outer sheath 200 is connected to inner sheath 100, either permanently or removably, in a manner that allows catheter 10 to be applied as a single unit to a male patient. In the illustrated example, the stem portion 132 of drainage port 130 passes through outer cap 210 with a substantially water- and air-tight connection or junction 212 between them. The sealed stem/cap connection at 212 can be achieved in different ways, for example with a tight sealing frictional (mechanical) fit between the material of stem 132 and a smaller diameter opening for the stem in outer cap 210; or by molding or insert-molding or otherwise forming or connecting the stem 132 integrally with the material of outer cap 210; or by sealing the exterior of the stem 132 to the surrounding wall of the outer cap 210 with a flexible waterproof adhesive; or with a separate gasket or seal; or in any other known manner. And, while a connection between stem 132 and outer cap 210 is currently preferred and illustrated as the connection between the inner and outer sheaths 100, 200, other forms of connection between the sheaths would be acceptable provided stem 132 can pass through outer cap 210 with a sealing fit.

Inner sheath 100, and in particular inner cap 110, is preferably spaced from the inside surface of outer sheath 200, and in particular from the inside surface of outer cap 210, so that an air space or volume S initially exists between at least the cap portions of the inner and outer sheaths.

Figure 7:
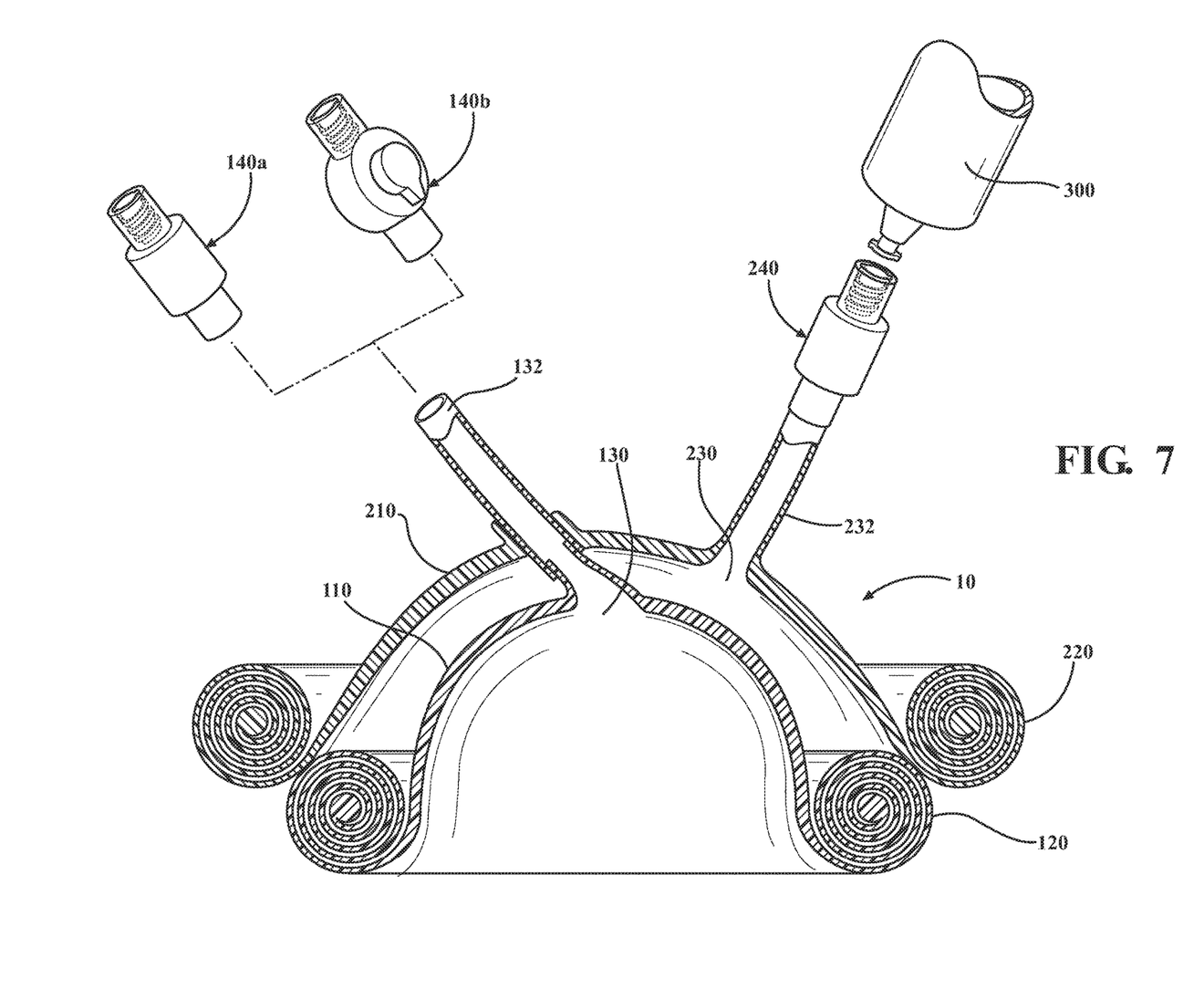
FIG. 7 is similar to FIG. 2, but showing some different one-way valve options for the drainage and suction ports in the device.

Each of inner drainage port 130 and outer suction port 230 has a one-way valve associated therewith, for example formed in or connected to the stem portions 132, 232 extending outwardly from suction cap 210 as illustrated, or coupled to the outer ends of the stem portions prior to the application of suction to the ports. Drainage port 130 includes a one-way valve 140, and suction port includes a one-way check valve 240. The illustrated valves 140,240 are shown in schematic form as ball-type valves of known type, optionally with a light bias-closing element such as a spring 141, 241 to help hold their respective ball valves or other closure elements 142, 242 in the closed condition against respective valve seats 144, 244 (FIG. 2). Those skilled in the art will recognize that different types of one-way valve may be used at 140 and 240, as known in the art of catheter devices and tubing, such as but not limited to thin membrane flap-type valves or umbrella-type valves. Other possible one-way valve mechanisms for 140 and 240 (shown schematically in FIG. 7) include "luer-lock" type valves commonly used with surgical tubing, opened automatically when a mating syringe or hose-coupling activating tip is coupled with the outer end of the valve, and closed automatically when the activating tip is removed, in known manner; or, manually operated valves with external handles or twist-lock bodies to open and close the valve. Whatever form they take, one-way valves 140, 240 allow the flow of air and/or liquid to be limited to one direction, i.e., outwardly from the inner and outer sheaths 100, 200 through their respective ports 130, 230 and stem/tubing structure 132, 232, and the valves may be automatically or manually controlled to limit the flow direction.

FIG. 2 illustrates one-way valve structure 140, 240 as being located inside continuous tubing used for at least the outer portions of stems 132, 142. The one-way valves could be connected to the tubing in other ways, for example in valve housings connected at their inlet and outlet ends to separate pieces of tubing that together form the stem passageways for air and liquid removal from the respective inner and outer sheath portions of the catheter device 10; or, to outermost ends of the stem portions 132, 142.

FIG. 2 shows the rolled body portions 120, 220 of the inner and outer sheaths rolled up to the lower perimeters of their respective sheaths. The diameter of outer sheath 200 is greater than the diameter of inner sheath 100, so that the cap portion 210 of the outer sheath overlies and surrounds at least an upper portion of the inner cap 110 of the inner sheath, and so that the inner and outer cap portions are connected in a way to create an air space S between them when initially applied. Also, it is preferred that the degree to which the outer cap 210 overlies/surrounds the inner cap 110 is limited, so that the rolled body portion 120 of the inner sheath is at least partially exposed underneath and can be easily accessed with fingers to be unrolled and applied over the wearer. The rolled body portions 120, 220 are generally more flexible than the structured caps, allowing them to be rolled up against their respective caps as shown in FIG. 2 prior to application on a patient, and then to be manually unrolled in the manner of a condom to extend down and seal around a patient's penis during application.

Figure 3:
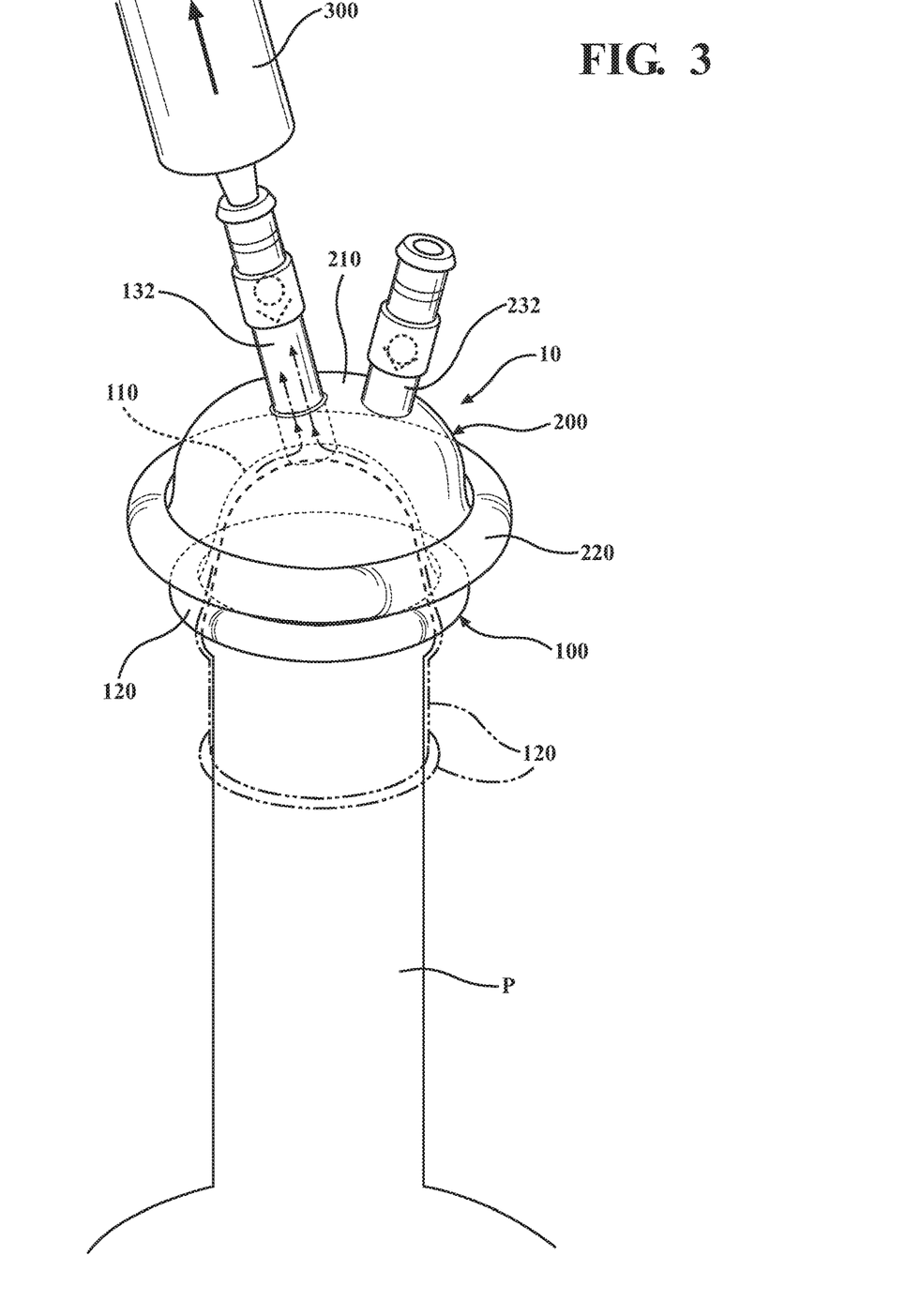
FIG. 3 shows the device of FIG. 1 partially applied over the head of the penis, wit suction being applied to a drainage port communicating with the drainage cap of the inner sheath portion and the rolled body of the inner sheath shown extended in phantom.

FIG. 3 shows an initial step in the method of applying catheter 10 to a patient or wearer. The inner cap 110 of catheter 10 is placed firmly on the top or head of a clean, oil-free penis P. A suction source or device 300, in the illustrated example shown as a syringe, is connected to drainage port 130 via stem 132, either before (preferred) or after the cap 110 is in place, and then suction is applied to pull air out of the cap 110 and draw the penis up into the inside of cap 110 in proximity to drainage port 130. With suction maintained on port 130, body portion 120 of inner sheath 110 is then unrolled down the shaft of the penis. Inner sheath body portion 120 is sized to be shorter when unrolled than outer sheath body portion 220, so that inner sheath body portion 120 extends only partway down the penis when fully unrolled.

FIG. 3 schematically illustrates one-way valve 140 in an open condition as the suction is applied by device 300, so that air can be evacuated from the inner cap 110 to create suction and a good fit of the head of the penis inside cap 110 near or against the drainage port 130.

Figure 4:
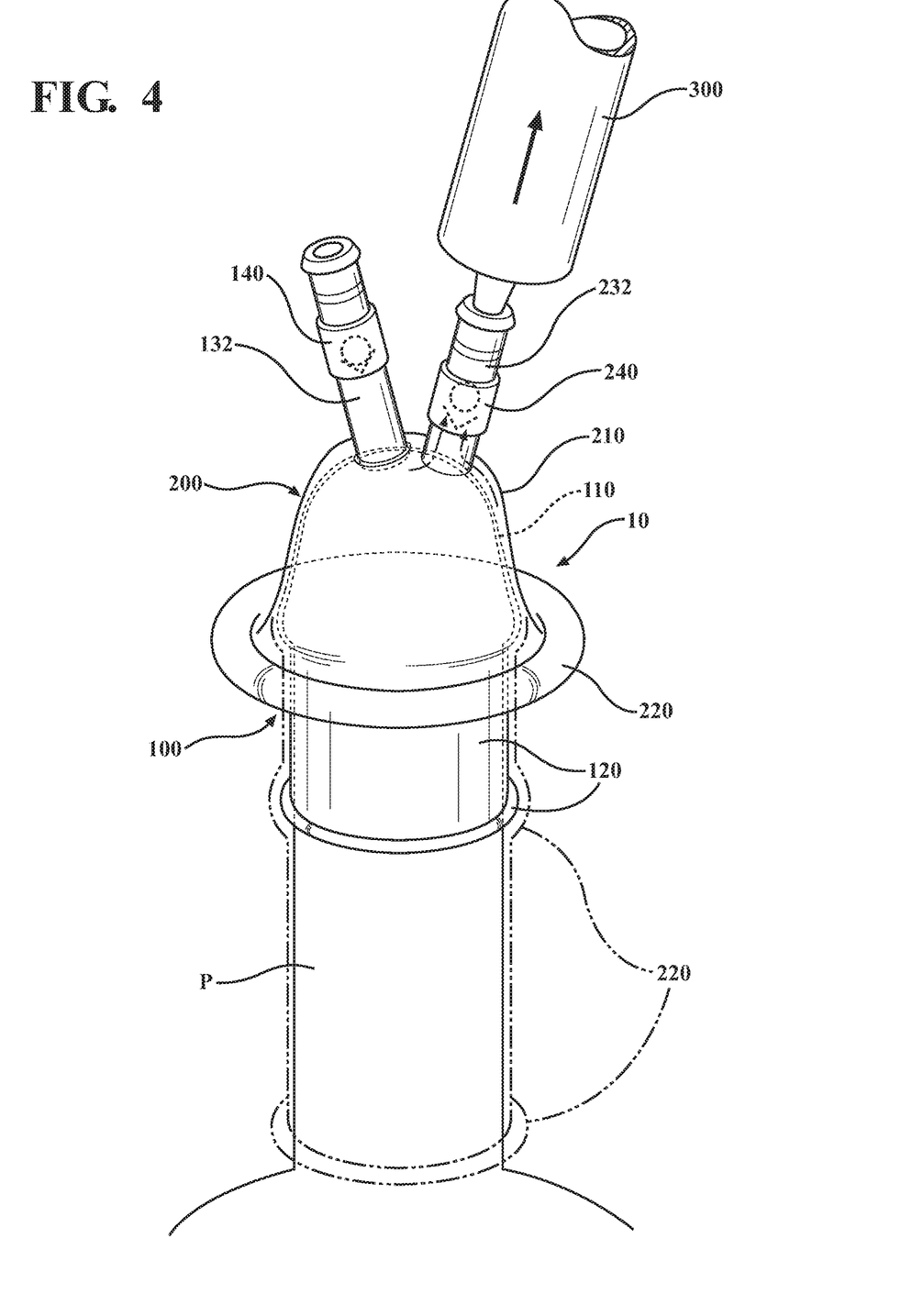
FIG. 4 shows the device of FIG. 1 as applied in FIG. 3, with the rolled body of the inner drainage sheath portion shown unrolled over the penis, suction being applied to the suction port communicating with the cap of the outer sheath portion, and the rolled body of the outer sheath shown extended in phantom.

Referring next to FIG. 4, once the inner sheath 100 is applied and secured as described above, the suction device 300 can be disconnected from port structure 130, 132 and the one-way valve 140 closed, in the case of an automatically-closing valve either under spring bias and/or due to the air pressure differential acting on the valve between the interior of the air-evacuated inner sheath/cap 100/110 and the outer open end of stem 132. In the case of a manually-operated valve, the valve 140 would be manually opened prior to applying suction, for example after the suction device is attached to the outer end of the valve/stem, and manually closed after the inner sheath has been satisfactorily evacuated to create a proper fit but before the suction device is removed.

Still referring to FIG. 4, a suction source or device such as 300 is connected to suction port 230 via stem 232, preferably without yet being activated during the initial application, and body portion 220 of the outer sheath is unrolled down the shaft of the penis over and beyond the lower end of unrolled inner sheath body portion 110, as far as possible down the shaft. Suction is then applied to port 230, for example by drawing back on the plunger (not shown) of the syringe, to open one-way valve 240 and remove most or all of the air from the space S between outer sheath 200 and inner sheath 100 and also from between the penis shaft and the outer sheath 200.

It might be necessary to apply suction in multiple cycles to the inner and outer sheaths in order to remove sufficient air to create the necessary vacuum for a secure fit at each stage of application. This may be accomplished, for example, by reapplying the suction device 300 to the respective port one or more times, each time drawing another plunger of air from the device until the desired vacuum or pressure differential is created to maintain a snug fit between the respective sheath and the penis. If the suction device needs to be disconnected between air-drawing or suction cycles, as might be necessary with a syringe, the one-way valves will serve to maintain the pressure differential by closing and preventing air from re-entering either of the sheaths.

Figure 5:
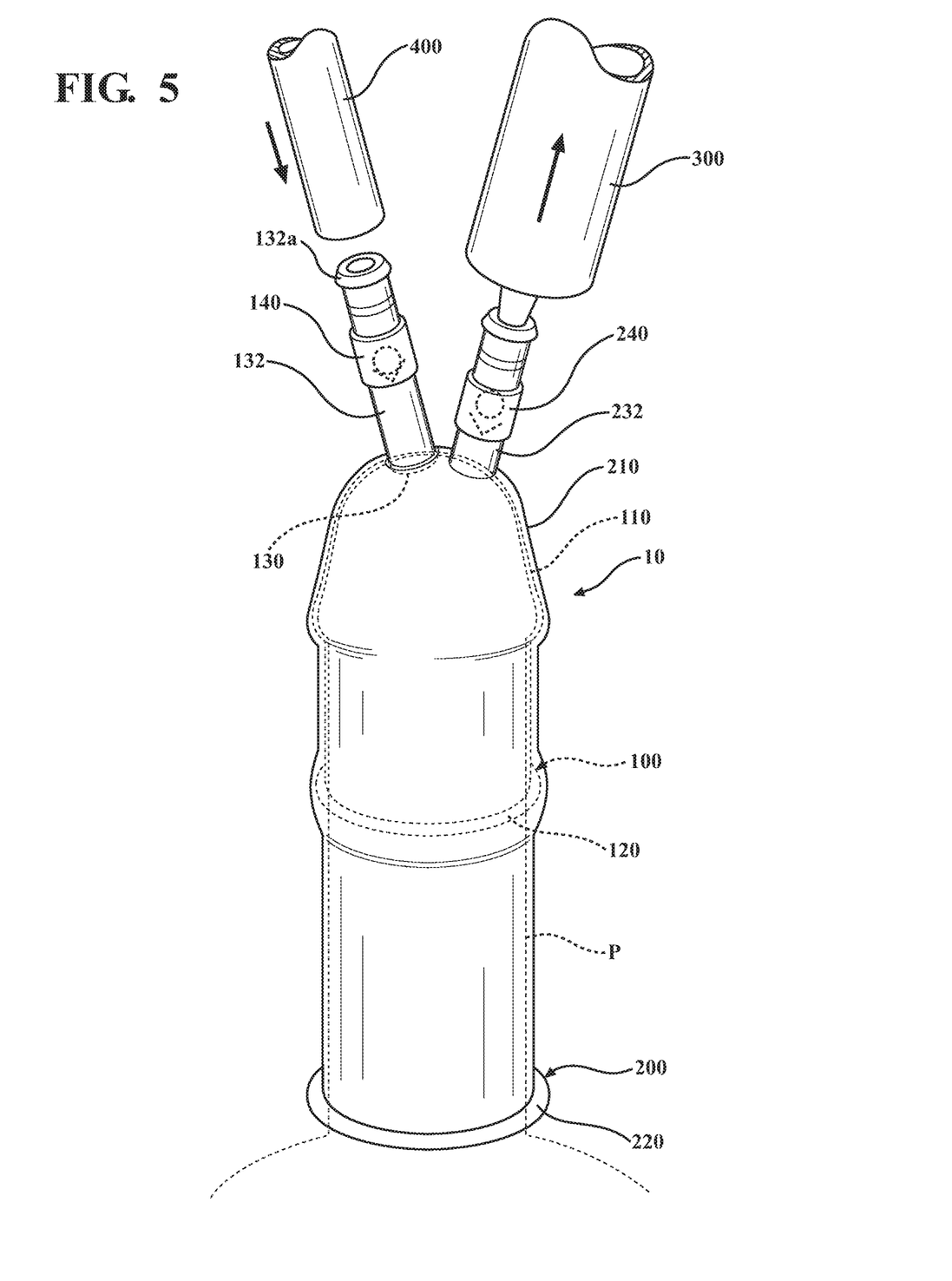
FIG. 5 shows catheter tubing being connected to the drainage port of the inner sheath while suction is maintained on the suction port of the outer sheath.

Referring to FIG. 5, it is important to create and maintain a strong suction or pressure differential between atmosphere and the interiors of the inner and outer sheaths 100, 200, and especially with respect to the outer sheath 200 after it is fully unrolled over the inner sheath, prior to drainage tubing 400 being applied to the outer end of drainage port stem 132. Once adequate self-maintaining vacuum or suction-fit is achieved for the outer sheath 200, the suction device 300 can be removed from stem 232 and the drainage tubing 400 connected to the inner sheath. Drainage tubing 400 can be any known type of hose or tubing used for catheters, and may be connected for example over a barbed flange 132*a* located on the outer end of stem 132, or to an exposed outer end of the one-way valve 140, in known manner.

It should be understood that once self-maintaining vacuum is achieved for the outer sheath 200, it is no longer necessary to maintain a one-way vacuum seal at the drainage stem 132, and the one-way valve 140 associated with the drainage port may be opened or removed, depending on the particular valve structure and its connection to the port/stem, so that urine may flow from the inner sheath without any resistance from the valve. The suction fit of the outer sheath 200 over the inner sheath 100 should be sufficient to maintain a good fit between the inner sheath 100 and the penis. Accordingly, the drainage port on inner sheath 100 may only need a one-way valve mechanism to maintain vacuum for the initial suction-fitting step, at least until the outer sheath 200 has been fitted over the inner sheath 100 with a desired suction-fit over the inner sheath 100 and the penis.

Figure 6:
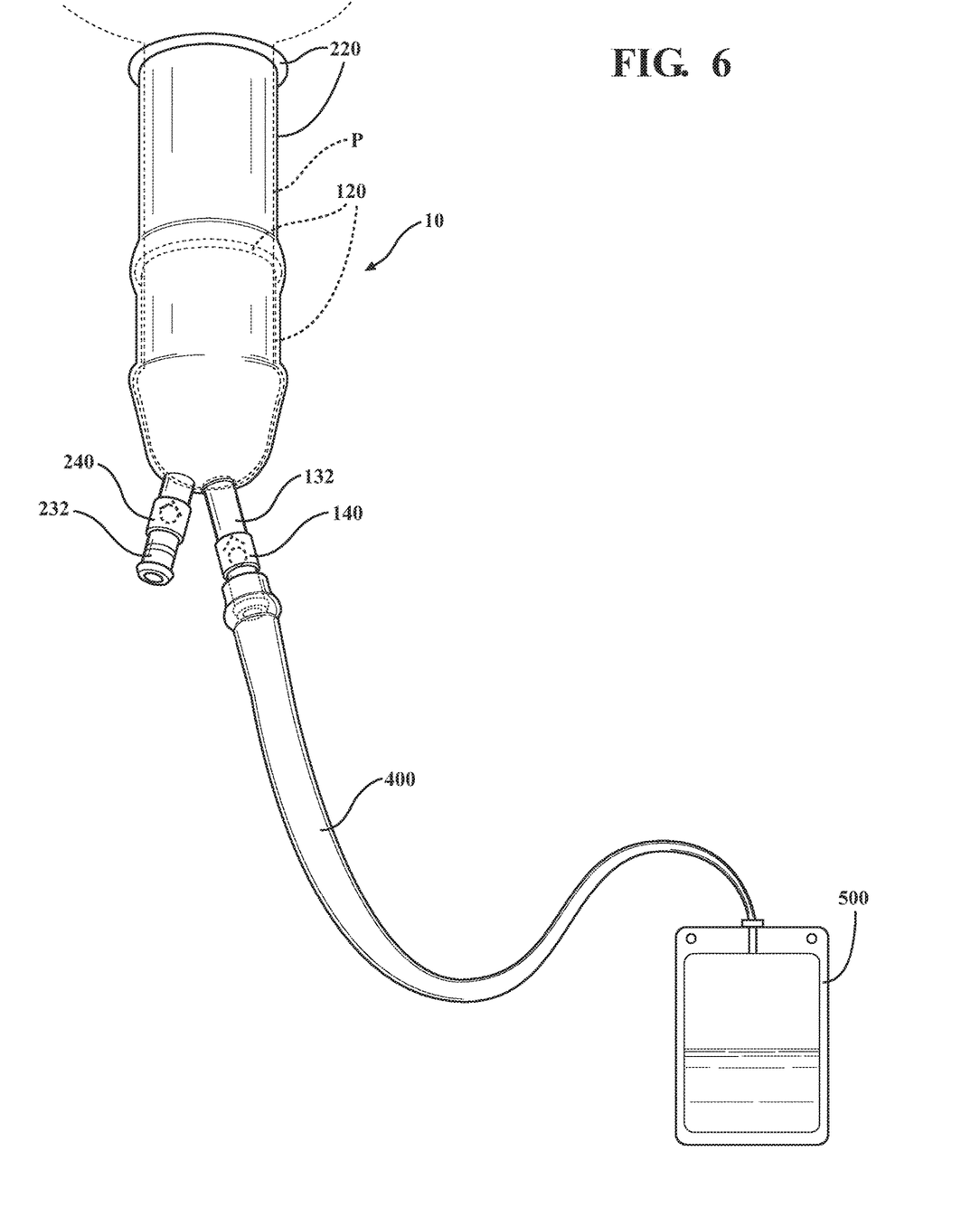
FIG. 6 shows the suction removed from the suction port of the outer sheath, and the catheter tubing communicating with a urine collection receptacle.

FIG. 6 shows catheter 10 applied to a male patient and in use, with the outer end of drainage tubing 400 connected to a urine collection receptacle 500, such as a sealed bag or other receptacle of known type for use with catheters. The self-maintaining suction in catheter 10, especially that between outer sheath 200 and the penis, maintains the inner sheath in position with the head of the penis near drainage port 130 in cap 110 of inner sheath 100, and keeps both the outer and inner sheaths 200, 100 firmly sealed around the penis, so that the catheter 10 as a whole remains firmly attached without fear of leakage. As noted above, valve 140 in the drainage port stem 130 may be selected from types that will suitably open automatically (as schematically shown in FIG. 6) to permit the passage of urine to tubing 400, for example by gravity or under pressure of urine flow, or that may be removed, or that may be opened manually with the fingers or a luer-type activating tip or drainage hose coupling.

It will finally be understood that the disclosed embodiments represent presently preferred examples of how to make and use the invention, but are intended to enable rather than limit the invention. Variations and modifications of the illustrated examples in the foregoing written specification and drawings may be possible without departing from the scope of the invention. It should further be understood that to the extent the term "invention" is used in the written specification, it is not to be construed as a limiting term as to number of claimed or disclosed inventions or discoveries or the scope of any such invention or discovery, but as a term which has long been used to describe new and useful improvements in science and the useful arts. The scope of the invention supported by the above disclosure should accordingly be construed within the scope of what it teaches and suggests to those skilled in the art, and within the scope of any claims that the above disclosure supports in this provisional application or in any non-provisional application claiming priority to this provisional application.

The invention claimed is:

1. An external male catheter, comprising:
    an inner drainage sheath portion comprising a structural drainage cap configured to conform to the shape of and receive the head of a penis and a flexible rolled drainage sheath connected to the bottom of said structural drainage cap, configured to be unrolled over a penis like a condom, and a drainage conduit extending upwardly and outwardly from said st drainage cap in flow communication with said inner drainage sheath below, such said drainage conduit can be connected alternatively to a suction source or alternatively to a drainage container;
    an outer suction sheath portion comprising a structural suction cap configured to conform to the shape of and be positioned over the head of a penis and an outer flexible rolled suction sheath connected to the bottom of said structural cap and configured to be unrolled over and in contact with said inner drainage sheath, said unrolled outer sheath extending downwardly past the bottom of said unrolled inner drainage sheath;
    said outer structural suction cap being positioned above, spaced from and connected to said inner structural drainage cap with said drainage conduit passing through said suction cap in a sealed junction such that said drainage conduit and said suction cap function independently of one another; said structural suction cap;
    including a suction conduit-extending upwardly and outwardly from said structural suction cap, spaced from said drainage conduit and in flow communication with said outer sheath below, whereby said suction conduit can be connected to a source of suction to suck said outer sheath tight against said inner sheath when a patient is urinating, thereby preventing leakage from said inner sheath during urination;
        said drainage conduit including a one way check valve such that when attachment of said external male catheter to the patient's penis is completed, the source of suction used in the attachment can be disconnected without releasing the suction which is holding said catheter in place;
        said suction conduit including a one way check valve such that said outer sheath will remain held tightly against said inner drainage sheath even if the source of suction is removed.

2. A method for applying said external male catheter of claim 1, comprising:
    applying said structural drainage cap to the head of a penis, or at the penis location if the penis is inverted; applying suction to said drainage conduit to draw the head of the penis positively into said structural drainage cap;
    unrolling said rolled flexible rolled drainage sheath over the shaft of the penis;
    unrolling said suction sheath downwardly over the shaft of the penis and over and beyond the bottom of said unrolled drainage sheath;
    connecting said suction conduit to a source of suction and applying suction to said suction conduit to evacuate air from between said drainage sheath and said suction sheath, and to secure said suction sheath over said drainage sheath and the penis with a suction fit; and,
    disconnecting said drainage conduit from said source of suction and connecting said drainage conduit to a urine collection receptacle;
    allowing said patient to urinate;
    disconnecting said drainage conduit from said urine collection receptacle and disconnecting said suction conduit from said source of suction;
rolling said suction sheath up to said structural suction cap and then rolling said drainage sheath up to said structural drainage cap and removing said external catheter from said patient.

3. A method for applying said external male catheter of claim 1, comprising:
    applying said structural drainage cap to the head of a penis, or at the penis location if the penis is inverted; applying suction to said drainage conduit to draw the head of the penis positively into said structural drainage cap;
    unrolling said rolled flexible rolled drainage sheath over the shaft of the penis;
    unrolling said suction sheath downwardly over the shaft of the penis and over and beyond the bottom of said unrolled drainage sheath;
    connecting said suction conduit to a source of suction and applying suction to said suction conduit to evacuate air from between said drainage sheath and said suction sheath, and to secure said suction sheath over said drainage sheath and the penis with a suction fit; and
    allowing said patient to urinate.

* * * * *